(12) United States Patent
Bader

(10) Patent No.: US 9,222,397 B2
(45) Date of Patent: Dec. 29, 2015

(54) METHOD AND DEVICE FOR CARRYING OUT A ZERO POINT ADAPTATION OF A LAMBDA PROBE OF AN INTERNAL COMBUSTION ENGINE

(75) Inventor: Dirk Bader, Renningen (DE)

(73) Assignee: Robert Bosch GmbH, Stuttgart (DE)

( * ) Notice: Subject to any disclaimer, the term of this patent is extended or adjusted under 35 U.S.C. 154(b) by 194 days.

(21) Appl. No.: 13/995,099

(22) PCT Filed: Dec. 2, 2011

(86) PCT No.: PCT/EP2011/071591
§ 371 (c)(1),
(2), (4) Date: Sep. 3, 2013

(87) PCT Pub. No.: WO2012/080000
PCT Pub. Date: Jun. 21, 2012

(65) Prior Publication Data
US 2013/0338902 A1    Dec. 19, 2013

(30) Foreign Application Priority Data
Dec. 15, 2010   (DE) .......................... 10 2010 063 095

(51) Int. Cl.
*F01N 11/00*     (2006.01)
*F01N 3/32*      (2006.01)
*F02M 25/07*     (2006.01)
*F02B 33/00*     (2006.01)
(Continued)

(52) U.S. Cl.
CPC *F01N 11/00* (2013.01); *F01N 3/32* (2013.01); *F02B 33/00* (2013.01); *F02B 39/10* (2013.01); *F02M 25/0718* (2013.01); *G01N 27/4175* (2013.01); *F01N 2560/025* (2013.01); *F02B 37/00* (2013.01); *F02D 41/0047* (2013.01); *F02D 41/1402* (2013.01); *F02D 41/1454* (2013.01); *F02D 41/2441* (2013.01); *F02D41/2454* (2013.01); *F02D 41/2474* (2013.01); *Y02T 10/121* (2013.01); *Y02T 10/20* (2013.01)

(58) Field of Classification Search
CPC ....... F02M 21/00; F02M 23/09; F02M 29/04; F02M 7/24; F02D 41/0042; F01N 13/14; F01N 11/00
USPC ........ 123/585–590, 698, 699, 26, 41 E, 65 B, 123/65 BA, 65 E, 703, 559.1, 559.2, 559.3, 123/562, 564, 565; 60/272–323, 607, 608, 60/624
See application file for complete search history.

(56) References Cited

U.S. PATENT DOCUMENTS 4,676,213 A * 6/1987 Itsuji et al. .................... 123/694
6,923,902 B2 * 8/2005 Ando et al. .................... 205/781
(Continued)

FOREIGN PATENT DOCUMENTS

WO    2008071500    6/2008

OTHER PUBLICATIONS

International Search Report for Application No. PCT/EP2012/071591 dated Mar. 14, 2012 (2 pages).

*Primary Examiner* — Lindsay Low
*Assistant Examiner* — Robert Werner
(74) *Attorney, Agent, or Firm* — Michael Best & Friedrich LLP

(57) ABSTRACT

The invention relates to a method for carrying out a zero point adaptation of a lambda probe (16) in an exhaust gas discharge section (4) of an internal combustion engine (2), wherein fresh air is pumped, during an after-run period following a deactivation of the internal combustion engine (2), from an air supply system (3) into the exhaust gas discharge section (4) such that fresh air flows around the lambda probe (16).

13 Claims, 4 Drawing Sheets

(51) Int. Cl.
*F02B 39/10* (2006.01)
*G01N 27/417* (2006.01)
*F02B 37/00* (2006.01)
*F02D 41/00* (2006.01)
*F02D 41/14* (2006.01)
*F02D 41/24* (2006.01)

(56) References Cited

U.S. PATENT DOCUMENTS

2009/0313990 A1* 12/2009 Mustafa .......................... 60/598
2011/0072792 A1* 3/2011 Bidner et al. .................... 60/278

\* cited by examiner

METHOD AND DEVICE FOR CARRYING OUT A ZERO POINT ADAPTATION OF A LAMBDA PROBE OF AN INTERNAL COMBUSTION ENGINE

BACKGROUND OF THE INVENTION

The invention relates to internal combustion engines which have a lambda probe in the exhaust tract for regulating the air/fuel ratio. The invention also relates to a method and to a device for carrying out a zero point adaptation of the lambda probe.

It is known for internal combustion engines, in particular Otto-cycle engines, to be provided with a lambda probe in the exhaust tract in order to determine the air/fuel ratio that was present at the time of the combustion in the cylinders. The lambda probe measures the residual oxygen content in the combustion exhaust gas and is used in a regulation means which regulates the ratio of fresh air to fuel of the air/fuel mixture supplied to the cylinders to a desired value through adjustment of the fuel quantity to be injected into the cylinders.

The normally used lambda probes are subject to drift owing to aging and the high temperature loading, such that adjustment of the lambda probe must be performed repeatedly. During said adjustment, the electrical variable (voltage) provided by the lambda probe is assigned to a certain oxygen concentration of the gas flowing past the lambda probe, and a corrective factor is determined by means of which the dependency between the electrical variable and the oxygen concentration can be calibrated.

Since, without feedback from a lambda probe, it is generally difficult to provide a defined air/fuel ratio in the cylinders, there is normally provided for this purpose an operating state in which fresh air is conducted past the lambda probe. The oxygen concentration of fresh air is approximately 21 vol % and is thus known, such that an unequivocal assignment of said measurement point of the lambda probe is possible.

In conventional internal combustion engines that are used in motor vehicles, there is generally provided, as an operating state, an overrun mode in which fresh air is conducted through the cylinders of the internal combustion engine without fuel being injected. The overrun mode arises when a driver of the motor vehicle releases the accelerator pedal and the engine is turned over by the mass inertia of the vehicle, without the engine itself generating a torque. With unchanged function of the inlet and outlet valves, fresh air then passes to the lambda probe after a few working cycles, such that the zero point adaptation can be carried out.

In the case of internal combustion engines operated in a so-called off-highway mode, such as for example internal combustion engines for driving generators, agricultural machines, machine tools and the like, an overrun mode is not provided because a moving mass sufficient to turn over the internal combustion engine is not provided. The operating state of the overrun mode, in which the zero point adaptation of the lambda probe can be carried out, is thus eliminated.

It is therefore an object of the present invention to provide a method for carrying out a zero point adaptation of internal combustion engines in the off-highway mode, and a corresponding engine system in which the zero point adaptation of the lambda probe can be provided in a simple manner.

SUMMARY OF THE INVENTION

Said object is achieved by means of the method for carrying out a zero point adaptation for a lambda probe of an engine system having an internal combustion engine, and by means of the engine system.

According to a first aspect, there is provided a method for carrying out a zero point adaptation of a lambda probe in an exhaust-gas discharge section of an internal combustion engine, wherein, during an after-run phase after a shut-down of the internal combustion engine, fresh air is pumped from an air supply system into the exhaust-gas discharge section, such that the lambda probe is immersed in fresh air.

One concept of the above method consists in utilizing existing or additional pumps in an engine system in order, in an after-run phase, that is to say after the shut-down of the internal combustion engine and before the shut-down of the control unit, to ensure that the lambda probe is immersed in fresh air. The zero point adaptation of the lambda probe can then be performed in accordance with known methods.

Furthermore, the after-run phase may follow a time at which the internal combustion engine comes to a complete standstill. In particular, the duration of the after-run phase may be limited in terms of time and last at least until the lambda probe has been immersed in fresh air.

In a further embodiment, a zero point adaptation of the lambda probe may be carried out as soon as the lambda probe has been immersed in fresh air.

According to a further aspect, an engine system is provided. The engine system comprises:
- an internal combustion engine to which fresh air can be supplied via an air supply system and from which combustion exhaust gas can be discharged via an exhaust-gas discharge section;
- a lambda probe which is arranged in the exhaust-gas discharge section;
- a pump for pumping fresh air from the air supply system to the exhaust-gas discharge section;
- a control unit for activating the pump, during an after-run phase after a shut-down of the internal combustion engine, in order to pump fresh air into the exhaust-gas discharge section such that the lambda probe is immersed in fresh air.

Furthermore, the pump may be arranged in a line which connects the air supply system to the exhaust-gas discharge section.

In particular, the pump may correspond to an exhaust-gas recirculation pump in an exhaust-gas recirculation line, wherein the exhaust-gas recirculation pump can be activated such that, in normal operation, it pumps combustion exhaust gas into the air supply system, in particular into an intake pipe portion, and such that, in the after-run phase, it is operated in a reverse mode in which fresh air is conducted into the exhaust-gas discharge section.

In a further embodiment, the pump may be arranged in a fresh air line which branches off from the air supply system in a region upstream of a compressor of a turbocharger and which opens into the exhaust-gas discharge section in the region of the lambda probe or upstream thereof.

Furthermore, the pump may correspond to a compressor, which can be operated independently of the internal combustion engine, of a turbocharger in the air supply system.

It may be provided that the control unit is designed to carry out a zero point adaptation of the lambda probe when the lambda probe has been immersed in fresh air.

BRIEF DESCRIPTION OF THE DRAWINGS

Preferred embodiments of the present invention will be explained in more detail below on the basis of the appended drawings, in which.

DETAILED DESCRIPTION

Figure 1:
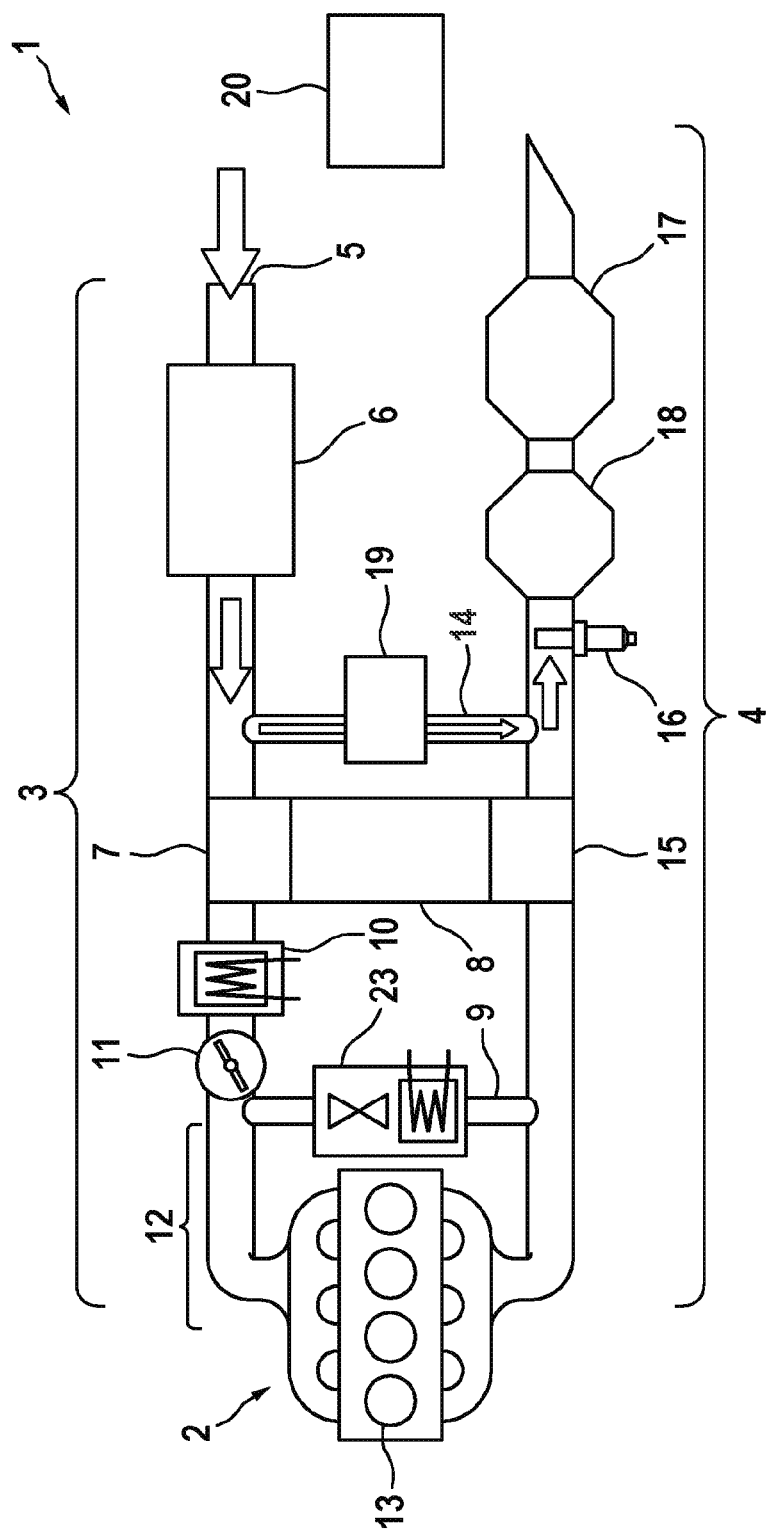
FIG. 1 is a schematic illustration of an engine system having an internal combustion engine, as per a first embodiment.

FIG. 1 shows an engine system 1 having an internal combustion engine 2 to which air is supplied via an air supply system 3 and from which combustion exhaust gas is discharged via an exhaust-gas discharge section 4.

The air supply system 3 comprises an intake opening 5 via which ambient air is sucked in, an air filter 6 which filters and removes particles from the inducted ambient air, and a compressor 7 for compressing the inducted and filtered fresh air. In the embodiment of FIG. 1, the compressor 7 is part of an exhaust-gas turbocharger 8. Downstream of the compressor 7 there is provided a charge-air cooler 10 for cooling the compressed fresh air which has been warmed as a result of the compression.

The amount of fresh air supplied to the internal combustion engine 2 can be adjusted by means of a throttle flap 11. In the present engine system 1, fuel can be injected either into an intake pipe portion 12 of the air supply system 3 or directly into the cylinders 13 of the internal combustion 2 in order to operate the latter.

The exhaust-gas discharge section 4 discharges the combustion exhaust gases from the internal combustion engine 2, which has generated said combustion exhaust gases by combustion of the air-fuel mixture in accordance with conventional four-stroke operation. A turbine 15 of the exhaust-gas turbocharger 8 is arranged in the exhaust-gas discharge section 4, said turbine being mechanically coupled to the compressor 7 in the air supply system 3. The exhaust-gas turbine 15 utilizes the exhaust-gas enthalpy of the combustion exhaust gas and converts said exhaust-gas enthalpy into compressor power for the compressor 7.

Between the intake pipe portion 12 and that part of the exhaust-gas discharge section 4 which is situated upstream of the turbine 15 there is provided an exhaust-gas recirculation line 9 in which an exhaust-gas recirculation valve 23 is provided for the purpose of supplying combustion exhaust gas as inert gas to the intake pipe portion 12. In this way, it is possible to realize a wider range of operating conditions of the internal combustion engine which serve for the optimization of combustion processes and the reduction of emissions.

Furthermore, a lambda probe 16 is arranged in the exhaust-gas discharge section 4 downstream of the turbine 15, by means of which lambda probe the oxygen content of the combustion exhaust gas can be determined. A particle filter 17 and a catalytic converter 18 may also be arranged downstream of the lambda probe 16.

The operation of the internal combustion engine 2 is controlled by a control unit 20. Based on state variables of the engine system 1, which are determined by means of suitable sensors such as for example an air mass sensor for detecting an air mass flow rate, a charge pressure sensor for detecting a charge pressure, a lambda probe for detecting a lambda value and the like, and/or which are modeled by means of system models, actuators such as for example a throttle flap actuator for adjusting the throttle flap, ignition times of ignition devices in the cylinders of the internal combustion 2, the efficiency of the turbocharger 8 and the like are controlled in order to activate the internal combustion engine in the desired way, that is to say so as to provide a desired drive torque.

Owing to aging and temperature influences, the lambda probe 16 is subject to considerable drift, such that a zero point adaptation of the lambda probe 16 must be carried out at regular intervals. During the zero point adaptation, the assignment of the electrical variable output by the lambda probe 16 to the oxygen concentration is corrected by means of a corrective factor. In general, said corrective factor is determined by determining the electrical variable output by the lambda probe 16 in the case of the lambda probe 16 being immersed in fresh air.

The operation of the internal combustion engine 2 and the zero point adaptation of the lambda probe 16 are carried out in a control unit 20.

In the case of engine systems which are used not in vehicles but rather in generators, agricultural machines, machine tools and the like, it is generally difficult to obtain fresh air without exhaust gas in the exhaust-gas discharge section 4. Whereas this is possible in the case of engine systems which are used in vehicles by means of an overrun mode, in which the engine is turned over, without fuel being injected, by the movement of the vehicle, such an operating state is not provided in the case of off-highway use of the engine system.

In order, for the zero point adaptation, to supply to the lambda probe a gas with an already known oxygen concentration, provision has hitherto been made to produce a state in which the lambda probe is immersed in fresh air. Since an overrun mode is not provided in the case of engines operated off-highway, fresh air is supplied to the lambda probe 16 in some other way in order to be able to carry out the zero point adaptation.

In the exemplary embodiment of FIG. 1, a branch is provided in the region of the air supply system 3, downstream of the filter 6, through which branch fresh air is conducted directly into the region of the exhaust-gas discharge section 4 at or directly upstream of the lambda probe 16. The fresh-air line 14 provided for this purpose is provided with an air pump 19 which is activated in order to pump fresh air into the exhaust-gas discharge section 4, such that the lambda probe 16 is immersed in fresh air.

Figure 2:
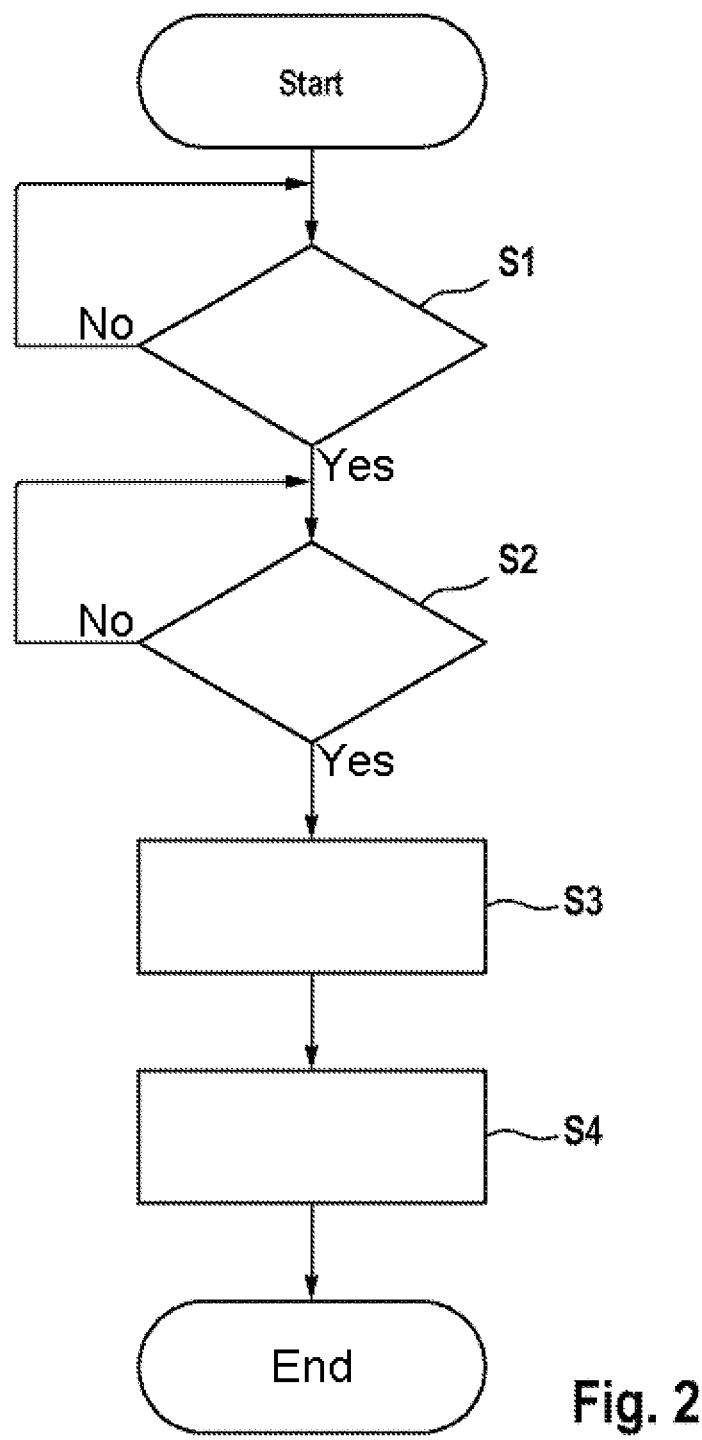
FIG. 2 is a flow diagram illustrating the method for carrying out the zero point adaptation on the basis of the embodiment of FIG. 1.

FIG. 2 is a flow diagram illustrating the method carried out for this purpose. Firstly, in step S1, it is detected whether the engine system 1 is in a shut-down state. If this is the case (alternative: yes), then it is detected in step S2 whether the internal combustion engine has come to a standstill; otherwise (alternative: no), the query of step S1 is repeated.

Upon the shut-down of the engine system 1, firstly the supply of fuel to the internal combustion engine 2 is interrupted, such that the internal combustion engine 2 runs down. If it is detected in step S2 that the internal combustion engine 2 has come to a standstill and is no longer moving (alternative: yes), then the method progresses to step S3; otherwise, the method waits at step S2 until the internal combustion engine 2 has come to a standstill.

The control unit 20 remains in operation even after the shut-down of the internal combustion engine 2, and in an after-run phase commencing when the internal combustion engine 2 comes to a standstill, activates the air pump 19 (step S3) in order to introduce fresh air into the exhaust-gas discharge section 4, such that the lambda probe 16 is immersed in fresh air. The duration of the after-run phase is defined such that it is ensured that an adequate amount of the lambda probe is immersed in fresh air in order to be able to carry out the zero point adaptation.

Subsequently, in step S4, the zero point adaptation of the lambda probe 16 can be carried out on the basis of the oxygen content of fresh air, such as is known from the prior art. During the zero point adaptation, a lambda value (voltage at the lambda probe) for an oxygen concentration of 21 vol % of the fresh air is measured, and from this a corrective factor and if appropriate a corrective offset is determined for the assignment function (generally approximately linear) of the lambda value to the actual oxygen concentration.

Figure 3:
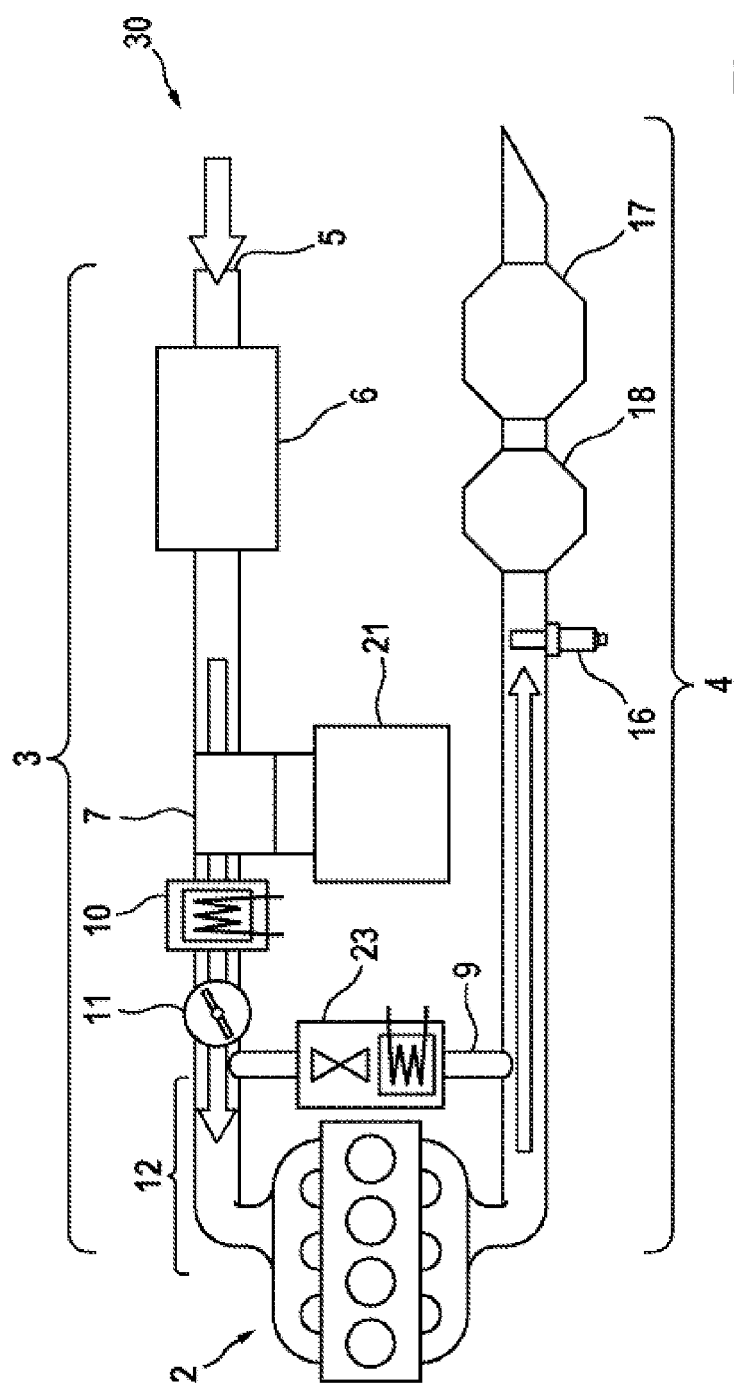
FIG. 3 is a schematic illustration of a further embodiment of an engine system for carrying out a zero point adaptation of the lambda probe.

FIG. 3 illustrates a further embodiment of an engine system 30. The engine system 30 of FIG. 3 corresponds for the most part to the engine system of FIG. 1. Instead of the fresh-air line 14, the air pump 19 and the exhaust-gas turbocharger 8, there is provided an electrically operated turbocharger with a turbocharger drive 21 which drives the compressor 7. In this way, it is possible for fresh air to be pumped through the air supply system 3 even after the internal combustion engine 2 has come to a standstill and when exhaust-gas enthalpy is no longer available.

The fresh air can be conducted through the recirculation line 9 and an open exhaust-gas recirculation valve 23 into the exhaust-gas discharge section 4. It is likewise possible in this way for the lambda probe 16 to be immersed in fresh air. The turbocharger drive 21 is set in operation or kept in operation in the after-run phase of the engine system 30, as described above, such that said turbocharger drive compresses fresh air and provides said compressed fresh air upstream of the compressor 7. The operation of the turbocharger drive 21 is preferably maintained until the lambda probe 16 has been reliably immersed in fresh air.

Figure 4:
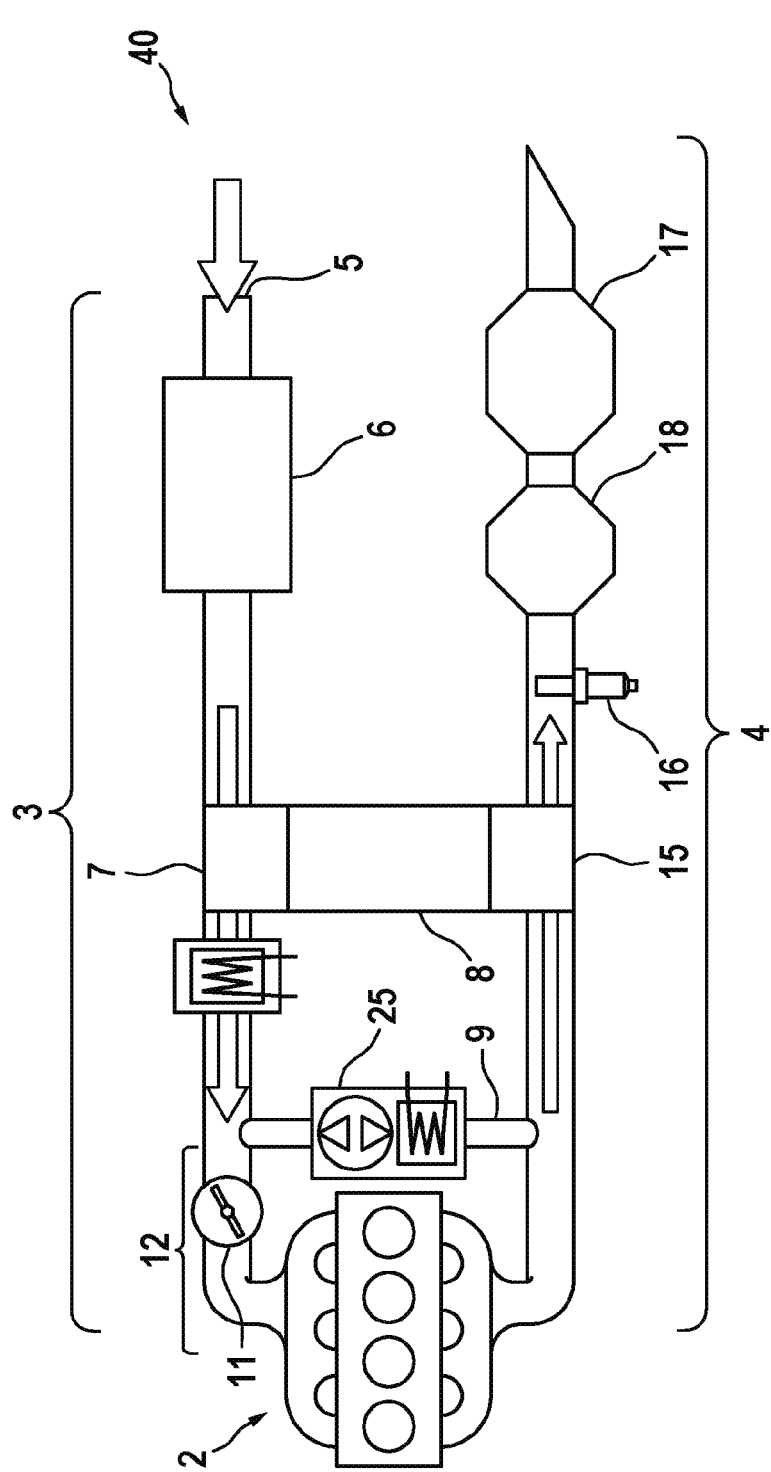
FIG. 4 is a schematic illustration of a further exemplary embodiment of an engine system for carrying out a zero point adaptation of the lambda probe.

Based on the embodiment of FIG. 1, the embodiment of FIG. 4 shows a further variant of an engine system 40, in which it is likewise possible to dispense with the fresh-air line 14 and the air pump 19. The embodiment of FIG. 4 relates to engine systems in which, instead of an exhaust-gas recirculation valve or in addition to the exhaust-gas recirculation valve, an exhaust-gas recirculation pump 25 is provided in the exhaust-gas recirculation line 9. The exhaust-gas recirculation pump 25 serves for actively pumping exhaust gas into the air supply system 3 during normal operation of the internal combustion engine 2.

To supply fresh air to the lambda probe 16 during the after run phase, it may now be provided that the exhaust-gas recirculation pump 25 can be operated in a reverse mode such that fresh air can be pumped from the air supply system 3 into the exhaust-gas discharge section 4. In this way, it is possible to dispense with the air pump 19 and the fresh-air line 14 and to use the already existing exhaust-gas recirculation pump 25 additionally for the zero point adaptation of the lambda probe 16.

The invention claimed is:

1. A method for carrying out a zero point adaptation of a lambda probe which is arranged upstream of a particle filter in an exhaust-gas discharge section of an internal combustion engine, the method comprising:
    during an after-run phase after a shut-down of the internal combustion engine, operating an exhaust-gas recirculation pump arranged in an exhaust-gas recirculation line, which directly connects the air supply system to the exhaust-gas discharge section, to pump fresh air from an air supply system into the exhaust-gas discharge section, without passing the fresh air through the cylinders of the internal combustion engine, such that the lambda probe is immersed in fresh air.

2. The method as claimed in claim 1, wherein the after-run phase follows a time point at which the internal combustion engine comes to a complete standstill.

3. The method as claimed in claim 1, wherein a duration of the after-run phase is limited in terms of time and lasts at least until the lambda probe has been immersed in fresh air.

4. The method as claimed in claim 1, wherein a zero point adaptation of the lambda probe is carried out when the lambda probe has been immersed in fresh air.

5. An engine system comprising:
    an internal combustion engine to which fresh air can be supplied via an air supply system and from which combustion exhaust gas can be discharged via an exhaust-gas discharge section;
    a lambda probe which is arranged upstream of a particle filter in the exhaust-gas discharge section;
    an exhaust-gas recirculation pump arranged in an exhaust-gas recirculation line which directly connects the air supply system to the exhaust-gas discharge section for pumping fresh air from the air supply system to the exhaust-gas discharge section, without passing the fresh air through the cylinders of the internal combustion engine;
    a control unit for activating the exhaust-gas recirculation pump such that, in normal operation, it pumps combustion exhaust gas into the air supply system, and such that, during an after-run phase after a shut-down of the internal combustion engine, it is operated in a reverse mode in order to pump fresh air into the exhaust-gas discharge section such that the lambda probe is immersed in fresh air.

6. The engine system as claimed in claim 5, wherein the pump is arranged in a fresh air line which branches off from the air supply system in a region upstream of a compressor of a turbocharger and which opens into the exhaust-gas discharge section in a region of the lambda probe or upstream thereof.

7. An engine system comprising:
    an internal combustion engine to which fresh air can be supplied via an air supply system and from which combustion exhaust gas can be discharged via an exhaust-gas discharge section;
    a lambda probe which is arranged upstream of a particle filter in the exhaust-gas discharge section;
    a compressor, which can be operated independently after the shut down of the internal combustion engine, of a turbocharger in the air supply system for pumping fresh air from the air supply system to the exhaust-gas discharge section, without passing the fresh air through the cylinders of the internal combustion engine;
    a control unit for activating the compressor, during an after-run phase after a shut-down of the internal combustion engine, in order to pump fresh air into the exhaust-gas discharge section such that the lambda probe is immersed in fresh air.

8. The engine system as claimed in claim 5, wherein the control unit is designed to carry out a zero point adaptation of the lambda probe when the lambda probe has been immersed in fresh air.

9. The engine system as claimed in claim 7, wherein the control unit is designed to carry out a zero point adaptation of the lambda probe when the lambda probe has been immersed in fresh air.

10. A method for carrying out a zero point adaptation of a lambda probe which is arranged upstream of a particle filter in an exhaust-gas discharge section of an internal combustion engine, the method comprising:

during an after-run phase after a shut-down of the internal combustion engine, operating a compressor, which can be operated independently after the shut down of the internal combustion engine, of a turbocharger in the air supply system, to pump fresh air from an air supply system into the exhaust-gas discharge section, without passing the fresh air through the cylinders of the internal combustion engine, such that the lambda probe is immersed in fresh air.

11. The method as claimed in claim 10, wherein the after-run phase follows a time point at which the internal combustion engine comes to a complete standstill.

12. The method as claimed in claim 10, wherein a duration of the after-run phase is limited in terms of time and lasts at least until the lambda probe has been immersed in fresh air.

13. The method as claimed in claim 10, wherein a zero point adaptation of the lambda probe is carried out when the lambda probe has been immersed in fresh air.

\* \* \* \* \*